United States Patent [19]

Biache

[11] Patent Number: 5,075,111
[45] Date of Patent: Dec. 24, 1991

[54] METHOD FOR THE BIOLOGICAL FIGHT AGAINST THE CROP RAVAGING INSECT, *PLUTELLA XYLOSTELLA*, USING A NUCLEAR POLYHEDROSE AND AT LEAST ONE SYNTHETIC PYRETHRINOID

[75] Inventor: Gërard Biache, Beynes, France

[73] Assignee: Calliope S.A., Beziers, France

[21] Appl. No.: 343,504

[22] Filed: Apr. 26, 1989

[30] Foreign Application Priority Data

May 2, 1988 [FR] France ............................ 88 05864

[51] Int. Cl.$^5$ ............................................ A01N 63/00
[52] U.S. Cl. ..................................................... 424/93
[58] Field of Search ........................................... 424/93

[56] References Cited

U.S. PATENT DOCUMENTS 4,668,511 5/1987 Aspirot et al. ...................... 424/93
4,911,913 3/1990 Hostetter ............................ 424/93

FOREIGN PATENT DOCUMENTS 2532522 3/1984 France .

OTHER PUBLICATIONS

"Microbial Control of Insects and Mites", H. D. Burges et al, pp. 497–499, 7/4/74.

Primary Examiner—Michael L. Shippen
Attorney, Agent, or Firm—Flynn, Thiel, Boutell & Tanis

[57] ABSTRACT

The present invention provides a method for the biological fight against the crop ravaging insect, *Plutella xylostella*, which consists of treating said crops with *Mamestra brassicae* nuclear polyhedrose and at least one synthetic pyrethrinoid.

14 Claims, No Drawings

METHOD FOR THE BIOLOGICAL FIGHT AGAINST THE CROP RAVAGING INSECT, *PLUTELLA XYLOSTELLA*, USING A NUCLEAR POLYHEDROSE AND AT LEAST ONE SYNTHETIC PYRETHRINOID

The present invention relates to a method for biologically fighting the crop ravaging insect, *Plutella xylostella*, using a nuclear polyhedrose and at least one synthetic pyrethrinoid.

*Plutella xylostella*, known also under the name of *Plutella maculipennis*, is a Crucifera ravager. Since the caterpillars of this ravager feed on plants on which they develop, attempts have been made at all times to fight against these harmful insects. For this, up to now, chemical insecticides have been used whose toxicity with respect to vertebrates in general and man in particular requires however strict precautions in use.

Thus, the Applicant has sought to perfect a new method of fighting against *Plutella xylostella*, using chemical insecticide doses which are considerably reduced with respect to those necessary, up to now, to destroy the ravager in question.

The Applicant has already had the occasion (see French patent no. 82 15097) to experiment, on lepidoptera noctuidae and in particular on *Mamestra brassicae, Spodoptera littoralis, Spodoptera frugiperda* and *Heliothis virescens*, with an insecticide composition containing, as active ingredient, a mixture formed by the nuclear polyhedrose of *Mamestra brassicae* and at least one photostable pyrethrinoid, the activity of this composition proving to be such that the pyrethrinoid and/or the polyhedrose could be used in reduced doses with respect to those recommended for application in the field of each of its constituents taken alone.

It will be recalled that, according to the systematic classification:

the Lepidoptera noctuidae form part of the family of noctuidae of section B of the sub-order of the Heteroceres, *Mamestra brassicae, Spodoptera littoralis, Spodoptera frugiperda* and *Heliothis virescens* coming into the groups of Trifinae and Quadrifinae, whereas *Plutella xylostella* is one of the species of the genus Plutella of the sub-family of the Plutellinae of the family of the Hyponomeutidae forming part of the family of the Tineidae entering into section D of the suborder of Heteroceres.

What precedes shows that the lepidoptera noctuidae ravagers and in particular *Mamestra brassicae, Spodoptera littoralis, Spodoptera frugiperda* and *Heliothis virescens* occupy in the systematic classification a position very much removed from that of *Plutella xylostella*.

Now, the Applicant has found that the insecticide composition described in the above mentioned patent no. 82 152097 was also active against *Plutella xylostella* and with reduced doses of pyrethrinoid with respect to those recommended for application of this pyrethrinoid alone in the field, so that in its use in the fight against *Plutella xylostella*, this composition is less toxic for the environment and can be handled more reliably than the use of a pyrethrinoid alone.

Revelation of the particularly interesting activity of this composition against *Plutella xylostella* is quite surprising from two points of view. First of all, it is surprising because of the very different nature of the lepidoptera noctuidae and *Plutella xylostella* because of their very much separated positions in the systematic classification. Also, it is surprising because of the great specificity of the viral action of nuclear polyhedroses; in this respect, it should be noted that at the doses recommended in the above French patent, the nuclear polyhedrose of *Mamestra brassicae* ($10^3$ polyhedres/ha) revealed itself quite insufficient for reducing the populations of the ravager *Plutella xylostella*. It is then apparent that nothing could lead to the assumption that the composition described in said French patent could have an insecticide activity against *Plutella xylostella*.

Consequently, a first object of the present invention is to provide a method for biologically fighting the crop ravaging insect, *Plutella xylostella*, this method being characterized in that it consists in treating said crops with the nuclear polyhedrose of *Mamestra brassicae* and at least one synthetic pyrethrinoid.

In a first variant of this method, said nuclear polyhedrose of *Mamestra brassicae* and said pyrethrinoid are used jointly and preferably in the form of a mixture.

In a second variant of said method, said nuclear polyhedrose of *Mamestra brassicae* and said pyrethrinoid are used successively, i.e. applied successively on the crop to be treated.

A second object of the invention resides in the use of a mixture of the nuclear polyhedrose of *Mamestra brassicae* and at least one synthetic pyrethrinoid for the preparation of an insecticide useful for the biological fight against the crop ravaging insect, *Plutella xylostella*.

The nuclear polyhedrose of *Mamestra brassicae* has been the subject of several fundamental studies which have made it possible to characterize it. We may mention for example Jurkovicova M., L. Van Toum, S. S. Sussenbach and J. Ter Shegget in Virology, vol 93, 1979, pages 8–19 as well as Vlak J. and A. Groner in Journal for Invertebrate Pathology, vol 35, 1980, pages 269–278.

Furthermore, a strain of the nuclear polyhedrose of *Mamestra brassicae* has been filed in the National Collection of Microorganism cultures at the Institut Pasteur (Paris) on Sept. 1st 1982 under the no. I-204. It should be further mentioned that a method of isolating the nuclear polyhedrose of *Mamestra brassicae* was described in detail in the French patent application no. 87 17748.

To provide as efficient a treatment as possible, it is preferable, in accordance with the invention, to choose the synthetic pyrethrinoid from among photostable pyrethrinoids. By way of examples of photostable synthetic pyrethrinoids the compounds of the following formula may be mentioned:

$$A-CO_2-CH(R) - \text{C}_6\text{H}_3(R_1) - O - \text{C}_6\text{H}_4(R_2) \quad (I)$$

in which=

R represents a hydrogen atom, an alkyl radical containing 1 to 4 carbon atoms, an alkynyl radical containing 2 to 8 carbon atoms or a nitrile group, $R_1$ and $R_2$ both represent a hydrogen atom or one represents a hydrogen atom and the other a fluorine or chlorine atom, and A represents:
a) either a radical:

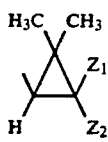

in which:
either $Z_1$ and $Z_2$ each represent a methyl radical,
or else $Z_1$ represents a hydrogen atom and $Z_2$ represents:
either a radical of formula:

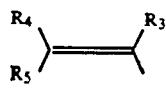

in which $R_3$ represents a hydrogen atom or halogen atom and $R_4$ and $R_5$, identical or different, represent a halogen atom or an alkyl radical containing from 1 to 8 carbon atoms or form together a cycloalkyl radical comprising from 3 to 6 carbon atoms or a radical:

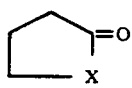

where the ketone is in $\alpha$ with respect to the double bond and in which X represents an oxygen or sulphur atom or a radical NH, or a radical of formula:

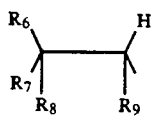

in which $R_6$ to $R_9$, identical or different, each represent a halogen atom,
b) or a radical:

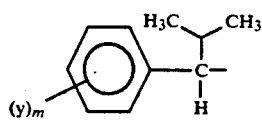

where Y represents a hydrogen atom, a halogen atom, an alkyl radical containing from 1 to 8 carbon atoms or an alkoxy radical containing from 1 to 8 carbon atoms and m=0, 1 or 2,
these compounds being in the form of one of their isomers or in the form of a mixture of their isomers. It will be noted that in the above formula (I): when R represents an alkyl radical, it is preferably the methyl or ethyl radical,
when R represents an alkynyl radical, it is preferably the ethynyl radical,
when $R_4$ and $R_5$ both represent a halogen atom, it is preferably the same halogen atom, $R_3$ and $R_6$ to $R_9$ preferably represent chlorine or bromine atoms,
when Y represents an alkyl radical, it is preferably the methyl, ethyl, i-propyl, n-butyl or t-butyl radical,
when Y, $R_4$ and/or $R_5$ represent a halogen atom, it is preferably a chlorine atom, and when Y represents an alkoxy radical, it is preferably the methoxy radical.

Among the photostable pyrethrinoids appropriate for the purpose of the invention, the following compounds will be mentioned in particular for which the common international name has been shown in brackets:

1R, cis 2,2-dimethyl 3-(2,2-dibromovinyl) cyclopropane carboxylate of (S) α-cyano 3-phenoxy benzyl (deltamethrine), dl cis trans 2,2-dimethyl 3-(2,2-dichlorovinyl) cyclopropane 1-carboxylate of RS α-cyano 3-phenoxy benzyl (cis/trans 30/10) (cypermethrine), dl cis trans 2,2-dimethyl 3-(2,2-dichlorovinyl) cyclopropane 1-carboxylate of RS α-cyano 3-phenoxy benzyl (90% of cis) (cypermethrine Hl cis), dl cis trans 2,2-dimethyl 3-(2',2'-dichlorovinyl) cyclopropane carboxylate of dl α-cyano (3-phenoxy 4-fluorophenyl) methyl (cyfluthrine), 2-parachlorophenyl 2-isopropylacetate of (S) α-cyano 3-phenoxy benzyl (fenvalerate), dl 2-(4-difluoromethyl oxyphenyl) 2-isopropyl acetate of dl α-cyano 3-phenoxy benzyl (flucitrinate), 1R, cis (2', 2', 2'-tribromo 1'-bromoethyl) 2,2-dimethyl cyclopropane carboxylate of (S) α-cyano 3-phenoxy benzyl (tralomethrine), 1R, cis (2',2'-dichloro 1',2'-dibromoethyl) 2,2-dimethyl cyclopropane carboxylate of (S) α-cyano 3-phenoxy benzyl (tralocythrine).

In accordance with the invention, the nuclear polyhedrose of *Mamestra brassicae* is advantageously used at a dose equal to or less than $1 \times 10^{13}$ polyhedres/ha and preferably at a dose of $1 \times 10^{12}$ to $5 \times 10^{12}$ polyhedres/ha. As for the pyrethrinoid, it is preferably formed by cypermethrine used at a dose of 2 to 10 g/ha.

The description of a number of experiments will be given hereafter as well as the results obtained.

As referred to earlier in the reference to French patent application No. 87/17748, the nuclear polyhedrose of *Mamestra brassicae* is isolated as follows.

EXAMPLE 1

Production of the Baculovirus of the Nuclear Polyhedrose of the Noctuid *Mamestra Brassicae*

*Mamestra brassicae* caterpillars are raised on an artificial nutritional medium (M) described in example 2, until the last but one larval stage. They are then infected by ingesting an artificial nutritional medium (M') described in example 3, contaminated by the baculovirus of the nuclear polyhedrose of the noctuid *Mamestra brassicae*. The contaminated caterpillars die within 9 to 10 days. The bodies are then crushed and filtered for example on a glass fiber filter having a mesh size capable of retaining all particles of a dimension greater than 0.3μ. On the filtrate, an acetonic precipitation is carried out by adding thereto four volumes of acetone for one volume of filtrate and lactose at the rate of 6% by weight of the filtrate and by subjecting the resultant mixture to energetic agitation for homogenizing it. As a variant, the filtrate may be lyophilized or subjected to spray drying. The power thus obtained contains the desired baculoviruses plus cellular waste. The activity of the preparations obtained as described above is determined by a series of counts using a hematimetric cell which makes it possible to count an average number of polyhedres, then by biological tests measuring the insecticide activity on caterpillars.

EXAMPLE 2

Composition of the Nutritional Medium (M) Mentioned in Example 1

For 1 kg of this nutritional medium, the following are used:

| Binders (A) | agar-agar | 16 g |
|---|---|---|
| | distilled water | 780 ml |

A/ EXPERIMENTATION IN THE FIELD

1. Equipment and Method Used for the Experiments

The nuclear polyhedrose of *Mamestra brassicae* used was obtained in a pilot manufacturing unit from *Mamestra brassicae* caterpillars fed on an artificial medium and infected at the 5th stage. This polyhedrose is used in a formulation called hereafter Mamestrin and whose titer is $2 \times 10^{12}$ polyhedres/liter. Mamestrin is applied by spraying in the form of an aqueous suspension comprising 5% of Mamestrin and 0.05% of Etaldyne (wetting agent).

The pyrethrinoid associated with the nuclear polyhedrose of *Mamestra brassicae* is cypermethrine, the pyrethrinoid-nuclear polyhedrose mixture being applied by spraying in the form of an aqueous suspension comprising 0.002% of cypermethrine, 1% of Mamestrin and 0.05% of Etaldyne.

Each experiment comprises a reference to a chemical insecticide, namely methomyl (trademark: LANNATE R WP 90) at the dose of 350 g/ha, used alone or with added deltamethrine (trademark DECIS of the French firm Procida) at the dose of 750 ml/ha.

All the tests were carried out on natural populations of the ravager *Plutella xylostella*, the area of the portions treated varying from 2000 m² to 1 ha. The plantations treated comprise either cauliflowers or cabbages. After the treatment, successive tests were made in time during which the number of living caterpillars of *Plutella xylostella* were counted.

The following table 1 shows the different experiments.

1. Results

These results appear in the following tables 2 to 4. Tables 2 and 3 show that the sensitivity of the *Plutella xylostella* caterpillars to the nuclear polyhedrose of *Mamestra brassicae* used at the dose of $1 \times 10^{13}$ polyhedres/ha and even at the stronger dose of $1.5 \times 10^{13}$ is very low, only Lannate offering a sufficient protection at the dose of 350 g/ha.

Table 4 shows that when the nuclear polyhedrose of *Mamestra brassicae* is used jointly with cypermethrine, on passing from treatment A to treatment C an increasing sensitivity can be seen of the *Plutella xylostella* caterpillars to the nuclear polyhedrose of *Mamestra brassicae*, for doses of cypermethrine of only 8 to 24 g/ha, which are without common measure with the very high doses of chemical insecticides recommended at present, such as those of treatment D. In particular, treatment C, which uses cypermethrine doses of 24 g/ha, gives a protection quite comparable to that obtained with the chemical insecticides used in treatment D at doses as high as 500 g/ha for Lannate and 750 ml/ha for Decis; this treatment C appears then as a treatment of choice in the fight against *Plutella xylostella*.

B/ LABORATORY EXPERIMENTATION

1. Method and Equipment

The nuclear polyhedrose of *Mamestra brassicae* is the same as that mentioned above for in-the-field experimentation. This polyhedrose, when it is used alone, is used in the form of an aqueous mixture comprising 20% of an aqueous suspension titrating at $72 \times 10^6$ polyhedres/ml and 0.05% of Etaldyne.

The chemical insecticide is fenvalerate and when it is used alone, it is in the form of an aqueous mixture comprising 8% of an aqueous suspension containing $1.67 \times 10^{-3}$ g/ml (or $1.67 \times 10^{-2}$) of fenvalerate and 0.05% of Etaldyne.

The combination of *Mamestra brassicae* nuclear polyhedrose and fenvalerate is used in the form of an aqueous mixture comprising 20% of an aqueous suspension titrating at $72 \times 10^6$ polyhedres/ml, 8% of an aqueous suspension containing $1.67 \times 10^{-3}$ g/ml of fenvalerate and 0.05% of Etaldyne.

The treatment was carried out by spraying on foliage (cabbage leaves). Each experiment was made at 25° C. and repeated four times on 50 *Plutella xylostella* caterpillars in stage $L_2$. Four days after the treatment, the percentage of dead caterpillars was recorded (taking into account the mortality of a control series—Abbot's correction) from stage $L_2$ to chrysalidation.

2. Results

The results obtained are as follows:

| | Mortality (%) |
|---|---|
| *Mamestra brassicae* | |
| nuclear polyhedrose (500 polyhedres/mm²) | 15 |
| Fenvalerate | |
| ($9 \times 10^{-9}$ g/mm²) | 9 |
| ($9 \times 10^{-8}$ g/mm²) | 70 |
| *Mamestra brassicae* | |
| nuclear polyhedrose (500 polyhedres/mm²) + Fenvalerate ($9 \times 10^{-9}$ g/mm²) | 54 |

These results show that the *Plutella xylostella* caterpillars are substantially insensitive to the nuclear polyhedrose of *Mamestra brassicae* alone. They also show that when fenvalerate is used alone at a dose of ($9 \times 10^{-8}$ g/mm²), it leads to a mortality rate of 70%, i.e. a mortality a little higher than that (54%) obtained by the association of the polyhedrose and of fenvalerate, the latter however being used in this association at a dose 10 times less. With the treatment of the invention, then, despite the small dose of fenvalerate used, it is possible to obtain protection against *Plutella xylostella* substantially comparable to that obtained when fenvalerate is used alone at a high dose.

With a view to the treatment, in accordance with the invention, of crops infested by *Plutella xylostella*, the nuclear polyhedrose of *Mamestra brassicae* and synthetic pyrethrinoid may in particular be used in the form of a powder, granules, suspensions, emulsions, or other formulations usually used in the field of insecticides, preferably in combination with other ingredients such as a vehicle such as water, alcohols, organic solvents; powders such as talc, clays, silicates or Kieselguhr; surface active agents for example nonionic surface active agents; or other pesticide agents.

It will be noted that the nuclear polyhedrose of *Mamestra brassicae* and the synthetic pyrethrinoid may be packed separately and used separately; as a variant, they may be packed separately, for example in the form of wettable powders for the polyhedrose and emulsifiable concentrates for the pyrethrinoid, then mixed before use, with the above mentioned ingredients.

TABLE 1

| Variant | (Equipment and method) Dose/ha | Number of treatments | Frequency (days) | Area |
|---|---|---|---|---|
| *1. First experimentation on cabbage crops* | | | | |
| Control | Not treated | — | — | 1 ha |
| Mamestrin | $1 \times 10^{13}$ polyhedres | 2 | 10 | 1 ha |
| Lannate | 350 g | 1 | — | 1 h |
| *2. Second experimentation on cauliflower, cabbage crops* | | | | |
| Control | Not treated | — | — | 3000 m² |
| Mamestrin | $1.5 \times 10^{13}$ polyhedres | 3 | 15 | 3000 m² |
| Lannate | 350 g | 3 | 15 | 3000 m² |
| *3. Third experimentation on cauliflower crops* | | | | |
| Control (T) | Not treated | — | — | 2000 m² |
| Mamestrin | $1 \times 10^{13}$ polyhedres | 2 | 7 | 2000 m² |
| Mamestrin + Cypermethrine | (A) $1 \times 10^{12}$ polyhedres + 8 g | 1 | 10 | 2000 m² |
| Mamestrin | $1 \times 10^{13}$ polyhedres | 1 | 7 | 2000 m² |
| Mamestrin + Cypermethrine | (B) $1 \times 10^{12}$ polyhedres + 8 g | 2 | 10 | 2000 m² |
| Mamestrin + Cypermethrine | (C) $1 \times 10^{12}$ polyhedres + 8 g | 3 | 7–10 | 2000 m² |
| Lannate + Decis | (D) 500 g + 750 ml | 2 | 14 | 2000 m² |

TABLE 2

(Results of the first experimentation)

| Variant | Number of living *Plutella xylostella* caterpillars found | | | |
|---|---|---|---|---|
| | 1 st test | 2 nd test | 3 rd test | 4 th test |
| Control | 12 | 85 | 12 | 3 |
| Mamestrin | — | 56 | 7 | 2 |
| Lannate | — | 12 | 8 | 2 |

TABLE 3

(Results of second experimentation)

| Variant | Number of living *Plutella xylostella* caterpillars found | | | | | |
|---|---|---|---|---|---|---|
| | test 1 | test 2 | test 3 | test 4 | test 5 | test 6 |
| Control | 63 | 113 | 194 | 147 | 51 | 0 |
| Mamestrin | 75 | 93 | 139 | 93 | 12 | 1 |
| Lannate | 60 | 105 | 44 | 45 | 23 | 2 |

TABLE 4

(Results of third experimentation)

| Variant | Number of living *Plutella xylostella* caterpillars found | | | | | |
|---|---|---|---|---|---|---|
| | test 1 | test 2 | test 3 | test 4 | test 5 | test 6 |
| Control = T | 1 | 77 | 198 | 50 | 13 | 0 |
| Treatment A | 3 | 98 | 116 | 18 | 8 | 1 |
| Treatment B | 0 | 66 | 45 | 6 | 1 | 0 |
| Treatment C | 1 | 8 | 8 | 1 | 0 | 1 |
| Treatment D | 0 | 7 | 4 | 4 | 2 | 1 |

I claim:

1. A method of protecting a crop against the crop ravaging insect, *Plutella xylostella*, characterized in that it consists in treating said crops with the nuclear polyhedrose of *Mamestra brassicae* and at least a synthetic pyrethrinoid, said nuclear polyhedrose of *Mamestra brassicae* being used in an amount sufficient to potentiate the insecticidal activity of said synthetic pyrethrinoid with respect to *Plutella xylostella*.

2. Method according to claim 1, characterized in that the *Mamestra brassicae* nuclear polyhedrose is used at a dose of from about $1 \times 10^{12}$ to $5 \times 10^{12}$ polyhedres/ha and said pyrethrinoid is cypermethrine used at a dose of 2 to 20 g/ha.

3. Method according to claim 1, characterized in that the *Mamestra brassicae* nuclear polyhedrose is used at a dose of $1\times10^{12}$ polyhedres/ha and said pyrethrinoid is cypermethrine used at a dose of 8 g/ha.

4. A method according to claim 1 in which the *Mamestra brassicae* nuclear polyhedrose is used at a dose of from about $1\times10^{12}$ to $5\times10^{12}$ polyhedres/ha and said pyrethrinoid is cypermethrine used at a dose of 2 to 10 g/ha.

5. A method according to claim 1 in which the *Mamestra brassicae* nuclear polyhedrose is used at a dose of $1\times10^{12}$ polyhedres/ha and said pyrethrinoid is cypermethrine used at a dose of 8 g/ha.

6. Method according to claim 1, characterized in that said nuclear polyhedrose of *Mamestra brassicae* and said pyrethrinoid are used jointly.

7. Method according to claim 1, characterized in that said *Mamestra brassicae* nuclear polyhedrose and said pyrethrinoid are used successively.

8. Method according to claim 1, characterized in that the synthetic pyrethrinoid is chosen from the photostable pyrethrinoids.

9. Method according to claim 8, characterized in that the pyrethrinoid is chosen from the following compounds:

1R, cis 2,2-dimethyl 3-(2,2-dibromovinyl) cyclopropane carboxylate of (S) α-cyano 3-phenoxy benzyl, dl cis trans 2,2-dimethyl 3-(2,2-dichlorovinyl) cyclopropane 1-carboxylate of RS α-cyano 3-phenoxy benzyl (cis/trans 30/10), dl cis trans 2,2-dimethyl 3-(2,2-dichlorovinyl) cyclopropane 1-carboxylate of RS α-cyano 3-phenoxy benzyl (90% of cis), dl cis trans 2,2-dimethyl 3-(2',2'-dichlorovinyl) cyclopropane carboxylate of dl α-cyano (3-phenoxy 4-fluoro phenyl) methyl, 2-parachlorophenyl 2-isopropylacetate of (S) α-cyano 3-phenoxy benzyl, dl 2-(4-difluoromethyl oxyphenyl) 2-isopropyl acetate of dl α-cyano 3-phenoxy benzyl, 1R, cis (2', 2', 2'-tribromo 1'-bromoethyl) 2,2-dimethyl cyclopropane carboxylate of (S) α-cyano 3-phenoxy benzyl, 1R, cis (2', 2'-dichloro 1',2'-dibromoethyl) 2,2-dimethyl cyclopropane carboxylate of (S) α-cyano 3-phenoxy benzyl.

10. Method according to claim 8, characterized in that the photostable synthetic pyrethrinoid is a compound of formula:

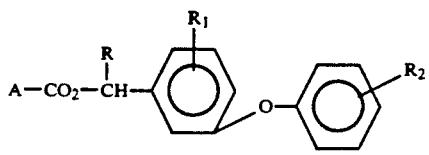  (I)

in which=

R represents a hydrogen atom, an alkyl radical containing 1 to 4 carbon atoms, an alkynyl radical containing 2 to 8 carbon atoms or a nitrile group, $R_1$ and $R_2$ both represent a hydrogen atom or one represents a hydrogen atom and the other a fluorine or chlorine atom, and A represents:

a) either a radical:

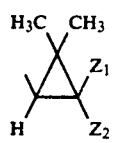

in which:

either $Z_1$ and $Z_2$ each represent a methyl radical,
or else $Z_1$ represents a hydrogen atom and $Z_2$ represents:
either a radical of formula:

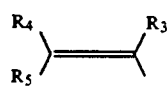

in which $R_3$ represents a hydrogen atom or halogen atom and $R_4$ and $R_5$, identical or different, represent a halogen atom or an alkyl radical containing from 1 to 8 carbon atoms or form together a cycloalkyl radical comprising from 3 to 6 carbon atoms or a radical:

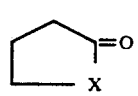

where the keto group is in α with respect to the double bond and in which X represents an oxygen or sulphur atom or a radical NH, or a radical of formula:

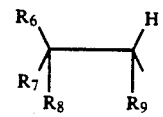

in which $R_6$ to $R_9$, identical or different, each represent a halogen atom, b) or a radical:

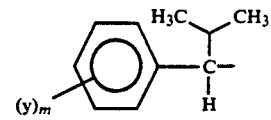

where Y represents a hydrogen atom, a halogen atom, an alkyl radical containing from 1 to 8 carbon atoms or an alkoxy radical containing from 1 to 8 carbon atoms and m=0, 1 or 2, this compound being in the form of one of its isomers or in the form of a mixture of its isomers.

11. Method according to claim 1, characterized in that the Mamestra brassicae nuclear polyhedrose is used at a dose equal to or less than $1 \times 10^{13}$ polyhedres/ha and in that the pyrethrinoid is cypermethrine used at a dose of 2 to 10 g/ha.

12. A method of treating a crop infected with the crop-ravaging insect, Plutella xylostella, which comprises treating the crop with an effective amount of an insecticide which is a mixture of the nuclear polyhedrose of Mamestra brassicae and at least one synthetic pyrethrinoid, said nuclear polyhedrose of Mamestra brassicae being present in said insecticide in an amount sufficient to potentiate the insecticidal activity of said synthetic pyrethrinoid with respect to Plutella xylostella.

13. A method as claimed in claim 12 in which said pyrethrinoid is a photostable synthetic pyrethrinoid of the formula:

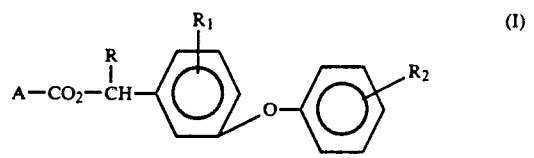  (I)

in which=

R represents a hydrogen atom, an alkyl radical containing 1 to 4 carbon atoms, an alkynyl radical containing 2 to 8 carbon atoms or a nitrile group, $R_1$ and $R_2$ both represent a hydrogen atom or one represents a hydrogen atom and the other a fluorine or chlorine atom, and A represents:

a) either a radical:

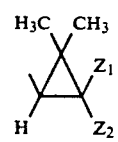

in which:

either $Z_1$ and $Z_2$ each represent a methyl radical, or else $Z_1$ represents a hydrogen atom and $Z_2$ represents:
either a radical of formula:

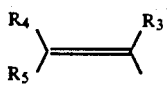

in which $R_3$ represents a hydrogen atom or halogen atom and $R_4$ and $R_5$, identical or different, represent a halogen atom or an alkyl radical containing from 1 to 8 carbon atoms or form together a cycloalkyl radical comprising from 3 to 6 carbon atoms or a radical:

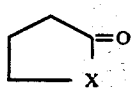

where the keto group is in α with respect to the double bond and in which X represents an oxygen or sulphur atom or a radical NH,
or a radical of formula:

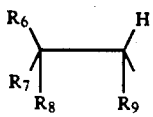

in which $R_6$ to $R_9$, identical or different, each represent a halogen atom,
b) or a radical:

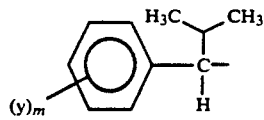

where Y represents a hydrogen atom, a halogen atom, an alkyl radical containing from 1 to 8 carbon atoms or an alkoxy radical containing from 1 to 8 carbon atoms and m=0, 1 or 2,
this compound being in the form of one of its isomers or in the form of a mixture of its isomers.

14. A method according to claim 12 in which the pyrethrinoid is selected from the group consisting of:
1R, cis 2,2-dimethyl 3-(2,2-dibromovinyl) cyclopropane carboxylate of (S) α-cyano 3-phenoxy benzyl,
dl cis trans 2,2-dimethyl 3-(2,2-dichlorovinyl) cyclopropane 1-carboxylate of RS α-cyano 3-phenoxy benzyl (cis/trans 30/10),
dl cis trans 2,2-dimethyl 3-(2,2-dichlorovinyl) cyclopropane 1-carboxylate of RS α-cyano 3-phenoxy benzyl (90% of cis),
dl cis trans 2,2-dimethyl 3-(2',2'-dichlorovinyl) cyclopropane carboxylate of dl α-cyano (3-phenoxy 4-fluorophenyl) methyl,
2-parachlorophenyl 2-isopropylacetate of (S) α-cyano 3-phenoxy benzyl,
dl 2-(4-difluoromethyl oxyphenyl) 2-isopropyl acetate of dl α-cyano 3-phenoxy benzyl,
1R, cis (2', 2', 2'-tribromo 1'-bromoethyl) 2,2-dimethyl cyclopropane carboxylate of (S) α-cyano 3-phenoxy benzyl,
1R, cis (2', 2'-dichloro 1',2'-dibromoethyl) 2,2-dimethyl cyclopropane carboxylate of (S) α-cyano 3-phenoxy benzyl.

* * * * *